United States Patent [19]

Inagaki et al.

[11] 4,246,908
[45] Jan. 27, 1981

[54] INTRACRANIAL PRESSURE TRANSDUCER

[75] Inventors: Hazime Inagaki; Masakazu Mizuno, both of Nagoya; Isemi Igarashi, Aichi, all of Japan

[73] Assignee: Kabushiki Kaisha Toyota Kenkyusho, Nagoya, Japan

[21] Appl. No.: 843,671

[22] Filed: Oct. 19, 1977

[30] Foreign Application Priority Data

Oct. 19, 1976 [JP] Japan .............................. 51-125804

[51] Int. Cl.³ .............................................. A61B 5/00
[52] U.S. Cl. ..................................... 128/748; 73/727; 73/728
[58] Field of Search ..................... 128/2.05 D, 2.05 E, 128/350 R, 672–675, 687–690, 748, 727–728; 73/726–728, 754

[56] References Cited

U.S. PATENT DOCUMENTS

| 3,031,591 | 4/1962 | Cory et al. ............................ 73/754 |
| 3,473,386 | 10/1969 | Nielsen, Jr. et al. ........... 128/2.05 D |
| 3,553,625 | 1/1971 | Stedman .......................... 128/2.05 D |
| 3,669,094 | 6/1972 | Heyer .................................. 128/2 R |
| 3,704,708 | 12/1972 | Iberall ............................. 128/2.05 E |
| 3,710,781 | 1/1973 | Hutchins et al. ..................... 128/675 |
| 3,810,459 | 5/1974 | Becker .................................. 128/2 V |
| 3,848,180 | 11/1974 | Jonke et al. ............................ 73/728 |
| 3,918,019 | 11/1975 | Nunn ...................................... 73/626 |
| 3,922,705 | 11/1975 | Yerman ................................... 73/626 |
| 4,023,562 | 5/1977 | Hynecek et al. ................. 128/2.05 E |
| 4,062,354 | 12/1977 | Taylor et al. ......................... 128/748 |
| 4,114,603 | 9/1978 | Wilkinson ............................. 128/2 R |

FOREIGN PATENT DOCUMENTS 1134712 10/1975 Japan .
1134713 10/1975 Japan .

OTHER PUBLICATIONS

Delaunois, A. L., "Low-Cost I.C. Transducer for Medical Pressure Measurements", MBE vol. 12, #3, May 1974, pp. 364–365.
Copper, R., "The Measurement of ICP," Brit. Jrnl. of Hospital Medicine, Nov. 1973, Equipment Supplement.
Gatz, A. J., "Manter's Essentials of Neuroanat. & Neurophys.," 4th Ed., 1970, F. A. Davis Co. Phil. pp. 124–127.
Barr, M. L., "The Human Nervous System," Harper & Row, N.Y., 1972, p. 360.
Eversden, I. D., "Modifier to a Min. Pressure Transducer for the Measurement of ICP," Med & Biol. Eng., 1970, vol. 8, pp. 159–164.
Mori, N., "A Study of Direct Measurement of Intra--Cranial Pressure," Nagoya Jrnl. Med. Sci., 1968, vol. 91, pp. 209–233.
Schettini, A. et al., "Simultaneous Pressure–Depth Measurement of the Intracranial System Mode Epidurally," Abstr. 2nd Inthal. Symp. on IC Pat Lund, Jun. 1974.
Tindall, G. T. et al., "Subdural Pressure Monitoring in Head-Injured Patients," ICP: Exper. & Clin. Aspects, edited by Brock & Dietz.
Hulem, A. L. et al., "A Technique for the Investigation of ICP in Man., J. Neurol., Neurosurg. Psychiot., 1966, vol. 29, No. 154.

Primary Examiner—Robert W. Michell
Assistant Examiner—Francis J. Jaworski
Attorney, Agent, or Firm—Oblon, Fisher, Spivak, McClelland & Maier

[57] ABSTRACT

An intracranial pressure transducer includes a casing comprising an annular member having a screwed part on an outer wall thereof for fitting and securing a skull of a body. A pressure-electric transducing portion including a supporting member which is inserted within an inner wall of the casing and is tightly fixed to the predetermined upper portion from a tip portion of the casing, an indicating circuit for indicating the intracranial pressure in response to an output of strain sensitive elements, and indicating means. The intracranial pressure transducer converts intracranial pressure of a cerebrospinal fluid to the internal pressure of a pressure receiving layer of the transducer by the copanar Coplanar method which maintains the dura to be coplanar by the depression of the pressure receiving layer of the transducer against the dura, applies internal pressure of the pressure receiving layer to a strain sensing member, supplies an electrical signal by a strain sensitive element in response to the internal pressure of the pressure receiving layer, and accurately and safely indicates the intracranial pressure on the indicating means.

20 Claims, 10 Drawing Figures

INTRACRANIAL PRESSURE TRANSDUCER

BACKGROUND OF THE INVENTION

1. Field of the Invention

This invention relates to an intracranial pressure transducer of a small size, which can accurately detect an internal pressure and a pulse pressure in a skull, without damaging a dura under a skull of a body to be measured.

2. Description of the Prior Art

The head of a human being or a body to be measured is of supreme importance for the life and social life thereof. The brain or cerebrum is retained in a container consisting of a skull and a spinal cord. This container is filled with a liquid which is referred to as a cerebrospinal fluid (C.S.F.), and the cerebrum floats in the liquid. An organism membrane referred to as a dura or duramater is present inside the skull for maintaining air tightness of a ventricle within the skull.

It is known in the field of cerebro-surgery and cerebro and neuro-surgery that an internal pressure within a skull is increased (intracranial pressure exacerbation) due to external causes such as a blow to the head of a human being, traffic accidents and the like, or internal causes such as epidural hemorrhage, encephaloma and the like. Such an increase in internal pressure in a skull is mainly attributable to an abnormal condition in the circulatory system of the cerebrospinal-fluid. When an increase in internal pressure in the skull affects a human body lightly, there occurs headache, dizziness, vomiting or the like. Further, when an increase in internal pressure in the skull severely affects a human body heavily, there results severe headache, consciousness loss, retardation of growth of the brain occuring from compression of the brain, anaerosis and the like.

In these fields, an internal pressure in a skull has been measured according to various methods for studying causes of a disease as well as for the maintenance of the life of a human body.

One of the methods for deriving an internal pressure information from the interior of a skull of a human body is to pierce an injection needle into a lumbar region of a body to be measured (lumbar puncture), and then a water level is measured by a water column manometer which is connected to the injection needle, for measuring an internal pressure in the skull.

This method is simple but suffers from inaccurate response to an internal pressure in a skull, because its measurement is carried out at the lumbar region apart a considerable distance from a head. Particularly in the case of internal pressure in a skull which is abnormally high, lumbar puncture results in a sharp reduction in intracranial pressure, and hence the brain is pushed down, with the result that the brain presses a circulatory system for a cerebrospinal fluid, thereby jeopardizing the life of a human body. This method is dangerous in most cases.

Recently, it has been a general practice for the measurement of an internal pressure in a skull to drill a hole in a skull cap and then to insert a tube into a ventricle by breaking a dura (dura-mater) under a skull for measuring a water level in a water column manometer connected to the tube. This method is advantageous only in view of the fact that an internal pressure in the skull is directly measured in a head. However, the dura should be broken to allow insertion of the tube and thus the brain is damaged, with an accompanying danger of cerebromeningitis due to microbism, as well as lack of safety.

When an internal pressure in a skull is further accurately measured, a high level of skill is required for a doctor, and considerable stress is imposed on a patient depending on a health condition (dying, weakness). Accordingly, the measurement for a long period of time appears impossible.

Recently, there has been proposed an electric-pressure transducer for accurately measuring an internal pressure in a skull in place of a water column manometer. In either case, the measuring method itself remains unchanged, so that the aforesaid shortcoming can not be avoided. As a result, an electrical pressure transducer for measuring an internal pressure in a skull has not yet reached a practical stage of clinical use, and fails to find a satisfactory use. There has arisen, accordingly, a demand for an electrical pressure transducer which overcomes the aforesaid shortcomings.

The measurement of an internal pressure and a pulse pressure in a skull of a human body according to the present invention is based on a discovery that an internal pressure as well as a pulse pressure within a skull can be measured without damaging an important dura according to the steps of: forcing a resilient, flat pressure-receiving layer, which houses a semiconductor pressure-electric transducing element, against a dura encompassing a brain under the skull; maintaining a balance between a force to press the dura or a pressure of a pressure receiving layer and a tension of the dura; and converting a pressure in a balanced condition which corresponds to an internal pressure and a pulse pressure in the skull into an electrical signal by the semiconductor pressure-electric transducing element. This intracranial pressure transducer provides a high degree of safety and is well adapted for use for periods of time, with an accompanying high accuracy in measurement.

The intracranial pressure transducer of the present invention comprises a casing including an annular member having a screwed part on an outer wall thereof for fitting and securing to a skull of a body, a pressure-electric transducing portion comprising a supporting member which is inserted within an inner wall of the casing and is tightly fixed to a predetermined upper portion from a tip portion of said casing, and which has a hole of predetermined diameter, a thin strain sensing member bonded to a lower surface of the supporting member having the hole in order to close the hole, at least one strain sensitive element for converting the strain of the strain sensing member to an electrical signal provided at a strain sensing region, which region corresponds to the hole of the supporting member, on the thin strain sensing member, lead wires connected to the strain sensitive element and a receiving connector provided at a top portion of the casing, and a pressure receiving layer comprising resilient material and filling a concave portion formed by an inner wall of the tip portion of the casing, the lower surface of the supporting member, and the lower surface of the thin strain sensing member, and an indicating circuit for indicating the intracranial pressure in response to an output of the strain sensitive elements, comprising an amplifier circuit connected to said lead wires within said pressure-electric transducing portion through connector means, and indicating means.

The intracranial pressure transducer having the above simple structure according to the present invention converts the intracranial pressure of a cerebrospinal fluid to the internal pressure of the pressure receiving layer by Coplanar method which maintains the dura to be coplanar by the depression of the pressure receiving layer of the transducer against the dura, applies the internal pressure of the pressure receiving layer to the strain sensing member, supplies the electrical signal by the strain sensitive element in response to the internal pressure of the pressure receiving layer, and accurately and safely indicates the intracranial pressure on the indicating means.

The present invention further provides for easier treatment and maintenance than prior intracranial pressure transducers utilizing a pressure chamber filled with fluid such as oil, which chamber is in contact to the strain sensing member. Generally, the pressure chamber of intracranial pressure transducer is formed with a rubber diaphragm and the rubber diaphragm is corroded by the oil. So, this transducer has a possibility of leakage of the oil from the hole and crack of the diaphragm within the body, and is defective with respect to human protection. Further, with this transducer, it is necessary to control the oil and it is troublesome to treat and maintain the same such that the life of the transducer is short.

On the other hand, in an intracranial pressure transducer having a metal diaphragm, accurate and stable measurement is impossible by directly detecting abnormal and concentrated pressure (stress) due to the projections and wave surface such as blood vessels of the dura.

The present invention easily solves these above-noted problems.

SUMMARY OF THE INVENTION

It is an object of the present invention to provide an intracranial pressure transducer which allows for a high accuracy and safety.

It is another object of the present invention to provide a practical intracranial pressure transducer of simple structure and easy treatment and maintenance.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENTS

Figure 1:
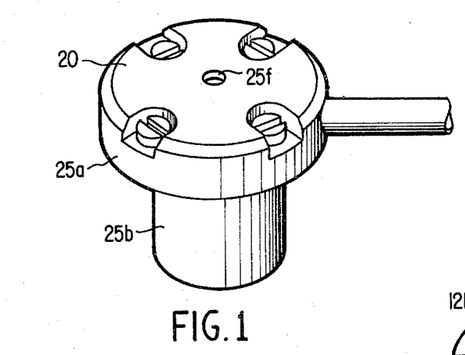
FIG. 1 is a perspective view of the pressure electric transducing portion in an intracranial pressure transducer according to the first embodiment of the invention.
Figure 2:
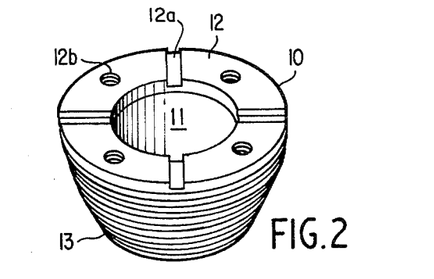
FIG. 2 is a perspective view of the adapter plug in the intracranial pressure transducer in the first embodiment.
Figure 3:
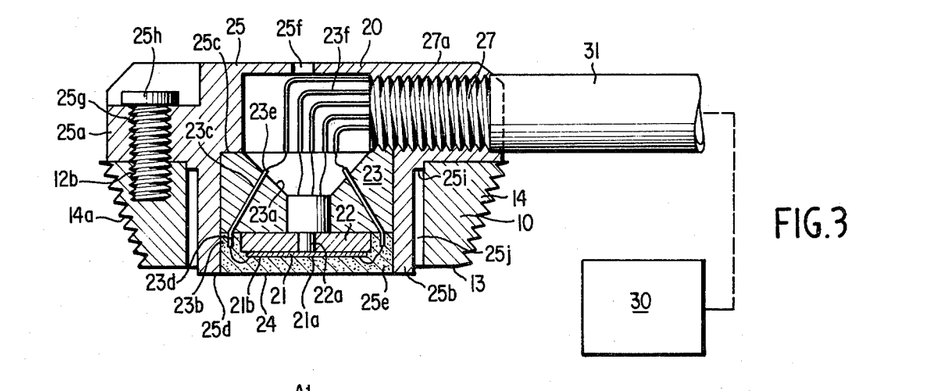
FIG. 3 is a cross-sectional view of the intracranial pressure transducer according to the first embodiment of the present invention.

The intracranial pressure transducer according to the first embodiment includes an adapter plug 10 as an adapter in the casing which is to be threaded into a hole drilled in the skull of a human body, a pressure-electric transducing portion 20 mounted in the adapter plug 10 for detecting an internal pressure and a pulse pressure under a skull as electrical signals, and an indicating circuit 30 connected to the pressure-electric transducing portion 20, for indicating an output signal of the pressure-electric transducing portion 20.

The adapter plug 10 is made of a stainless steel, while a through-hole or an inner hole 11 concentric with the center axis of the plug 10 is provided in the adapter from a top surface 12 to a bottom surface 13 of the adapter. The diameter of the through-hole or inner wall 11 is slightly larger than the outer diameter of an annular leg portion of a case member 25 as a case member in the casing for enclosing the pressure-electric transducing portion 20 which will be described later. The casing in this first embodiment comprises an adapter comprising the adapter plug 10, and a case member comprising the case member 25.

The top end surface 12 is an annular flat surface, with channels or grooves 12a extending crosswise from the center axis of the through hole 11 in the radial direction. Each of the grooves 12a is connected to the outer periphery and the inner periphery of the adapter. Thus, an exterior of the adapter 10 is communicated with the through-hole 11 through the channels 12a.

Blind screw holes 12b are provided at equal space intervals in the flat top surface 12 for threadedly securing the pressure-electric transducing portion 20 to be described later.

The outer peripheral wall of the adapter plug 10 tapers as shown at numeral 14 from the top surface 12 towards the bottom surface 13 thereof, while threads 14a are formed on the taper 14 which is to be the outer peripheral surface of the adapter plug 10, thereby facilitating threaded attachment of the adapter 10 to a skull of a head of a body to be measured. The pressure-electric transducing portion 20 is mounted in the through-hole 11 in the adapter plug 10.

The pressure-electric transducing portion 20 incorporates a semi-conductor strain-electric transducing element (this will be referred to as a strain sensitive element, hereinafter) which utilizes a piezoresistive effect of a semiconductor. The pressure-electric transducing portion 20 includes a pressure-electric transducer 24 which includes a thin strain sensing member 21 of a silicon single crystal, a first supporting member 22 bonded to a back surface of the strain sensing member 21 (not provided with strain sensitive elements), for supporting same, and a second supporting member 23 bonded to a back surface of the first supporting member 22 for supporting same. The transducer 24 is mounted in a case member 25. Provided on the surface of the pressure-electric transducing portion 20 is a thin, resilient pressure receiving layer 25e having a given pressure receiving surface to be in contact with a dura under the skull, thereby providing a pressure transmitting portion. In addition, a passage defined by the inner wall of the first and second supporting members 22, 23 is provided on a side opposite to the pressure receiving surface as the pressure transmitting portion of the strain sensing member 21 for introducing an atmospheric pressure thereto, so that an external pressure (intracranial pressure through the dura) acting on the pressure receiving surface of the pressure receiving layer 25e can be transmitted to the strain sensitive element 21a on the strain sensing member 21 as the internal pressure of the pressure receiving layer as a Coplanar method, and thus an electrical output signal of the strain sensing element 21a is taken out through a connector 27.

More specifically, the strain sensing member 21 of a semiconductor silicon single crystal is a super-miniature, super-thin type pressure-electric transducing element developed in the inventors' laboratory, and the dimensions of the member 21 is 0.038 mm thickness, 5 mm width×6 mm length, forming a rectangle. Integrally formed on a silicon base as a strain sensing member 21 according to a diffusion method are two pairs of P-type silicon strain sensitive elements 21a (positioned in the center), signal transmitting portions contiguous thereto, and electrode portions 21b contiguous to the signal transmitting portion. The aforesaid pressure electric transducing element affords a high sensitivity which allows the detection of a pressure up to 0.5 atm. The central part of the member 21 is etched and formed to a thickness of $50\mu$. Thus, the pressure-electric transducer 24 according to the present invention uses the pressure-electric transducing element having a high sensitivity as a strain sensing member 21.

The peripheral portion of the strain sensing member 21 (not provided with strain sensitive elements 21a) is bonded to the first supporting member 22, while a central portion thereof (provided with the strain sensitive elements 21a) is not bonded thereto. The central portion thereof is used as a strain sensing portion adapted to be deformed under a pressure. Accordingly, the strain sensitive element 21a integrally formed with the strain-sensing portion of the strain sensing member 21 causes a variation in electrical signal based the piezoresistive effect, proportional to a magnitude of strain of the strain sensing portion, which magnitude in turn is proportional to the level of a pressure.

The first supporting member 22 is made of a crystallization glass having the same thermal expansion rate as that of the strain sensing member 21. The first supporting member is shaped as an square member having a through-hole 22a of a circular cross section in its central portion. The strain sensing member 21 is bonded to the periphery of through-hole 22a of a circular cross section so as to close the through-hole 22a by the strain sensing member 21, thereby minimizing the influence of an ambient temperature change on the strain sensing member 21.

The second supporting member 23 is made of stainless steel and greater in thickness than the first supporting member 22. The member 23 has an outer diameter larger than that of the first supporting member 22, so as to tightly fix member 23 to the inner wall of the case member 25, and a funnel-shaped through-hole 23a. The funnel-shaped through-hole 23 comprises a through-hole in its central portion, whose diameter is slightly larger than that of the central through-hole 22a in the first supporting member 22, and a tapered through-hole provided in the upper portion of the second supporting member 22 which is continuous with the central through-hole of the member 23. The funnel-shaped through hole 23a is continuous with the through-hole 22a in the first supporting member 22 in concentric relation thereto. In this manner, the second supporting member 23 of an annular form is bonded to the first supporting member 22.

Five through-holes are provided at suitable circumferential spaces in the second supporting member 23 in a manner to extend into a portion 23b defined between the second supporting member 23 and the outer peripheral surface of the first supporting member 22 along the circumference of the first supporting member 22. In addition, lead pins 23c are inserted into the aforesaid through-holes, with head portions 23d of the lead pins 23c protruding into the aforesaid portion 23b contiguous to the second supporting member 23. One end of each lead pin 23c is connected to a lead wire connected to each of electrode portions 21b on the strain sensing member 21, while the end 23e of each of the lead pins 23c protrudes into the tapered through-hole of a large diameter of the funnel-shaped through-hole 23a, which is positioned inwardly of the second supporting member 23, and is connected to each of lead wires 23f which is then connected to a terminal of a connector 27.

As has been described earlier, the pressure-electric transducer 24 including the strain sensing member 21, and first and second supporting members 22, 23 is accommodated in the case member 25 as shown in FIG. 3.

The case member 25 is made of stainless steel and is provided with an annular flange portion 25a at the upper portion thereof, and a hollow annular depending portion 25b protruding downwards. The inner peripheral surface of the case member 25 is formed with a circumferentially stepped portion 25c, while an upper internal hole above the stepped portion 25c is concentric with a lower internal hole under the stepped portion 25c in the form of a cylindrical hole. In this respect, the inner diameter of the upper internal hole is smaller than that of the lower internal hole, while the inner diameter of the lower internal hole is substantially the same as the outer diameter of the second supporting member 23, so that the pressure-electric transducer 24 is seated on the stepped portion in a stable manner.

A very small space defined by the top surfaces of the strain sensing member 21 of the pressure-electric transducing portion 20, and first and second supporting members 22, 23, plus the inner surface of the annular leg portion 25b of the case member 25, is filled with silicone resin in the form of a thin membrane up to the level of the end face 25d of the annular leg portion 25b of the case member 25, thereby forming a pressure receiving layer 25e (0.5 mm thickness) having a resiliency (about 5 kg/cm$_2$) in such a space. The pressure-receiving layer 25e can detect an external pressure (intracranial pressure) as the internal pressure due to Coplanar method and apply a pressure thus detected to the strain sensing member 21 in the aforesaid pressure-electric transducing portion 20, thus serving as a pressure transmitting cell.

The outer top surface of the case member 25 is chambered or of a flat frustoconical shape (a frustum of a cone), while a communicating-hole 25f is provided in the top flat surface thereof in its center portion for communication between the exterior and the interior of the casing, so that an atmospheric pressure can be introduced into the interior of the casing.

The undersurface of the annular flange portion 25a, provided from the upper outer peripheral portion of the case member 25, is flat, while the width of flange portion 25a is equal to the width of the top surface 12 of the adapter plug 10. In addition, through-holes 25g for bolts 25h are provided at angularly equal spaces around the top outer peripheral portion of the flange portion 25a in register with the blind screw holes 12b provided at equal angular spaces in the top surface 12 of the adapter plug 10 along its circumference. Thus, bolts 25h can be inserted through the holes 25g and 12b for threadedly fastening the case member 25 to the adapter plug 10.

Formed on the outer peripheral surface of the annular leg portion 25b is a circumferentially stepped portion 25i whose diameter is smaller than that of the flange portion 25a but whose diameter is larger than that of the outer perifery of the annular leg portion 25b, with the result that, when the annular leg portion 25b is fitted in the adapted plug 10, there is formed a cylindrical clearance 25j between the inner peripheral surface of the adapter plug 10 and the outer peripheral surface of the annular depending portion 25b. The clearance 25j is communicated with respective channels 12a provided in the top surface 12 of the adapter plug 10, for discharging a fluid such as blood exuded during the operation to the exterior of the pressure-electric transducing portion 20 thereby bringing the interior and the exterior of the casing into mutual communication.

In addition, the length from the undersurface of the flange portion 25a to the undersurface of the annular leg portion 25d is greater than that of the adapter plug 10 which covers from the top end face 12 to the top 12, so that the tip 25d of the annular leg portion 25b protrudes from the tip 13 of the plug 10 a predetermined length.

Meanwhile, a connector 27 is provided with a screw portion 27a at one portion thereof and the screw portion 27a is threaded into a screw hole provided in the side wall of the case member 25, so that terminals of the connector 27 which are positioned internally of the case member 25 are connected to the aforesaid lead pins 23c via lead wires 23f, while a plug 31 for the indicating circuit 31 is connected to the other end of the connector 27, which plug protrudes from the case member 25 outwardly, so that an electrical signal based on an internal pressure and a pulse pressure in the skull can be derived through the connector 27.

Figure 4:
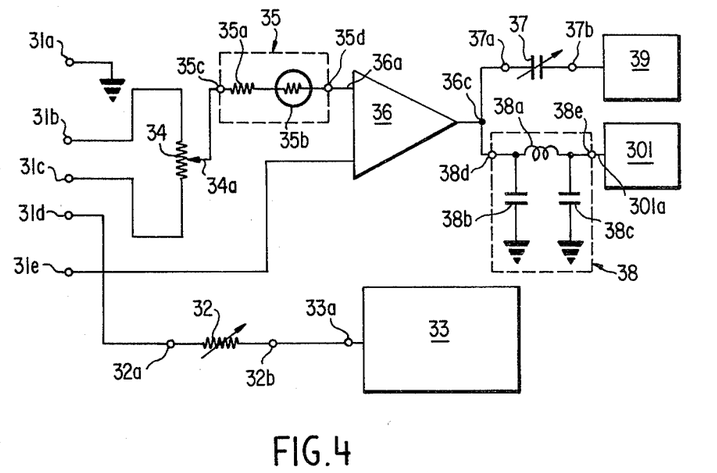
FIG. 4 and FIG. 5 are block diagrams of the indicating circuit for the intracranial pressure transducer according to the embodiment of the invention.

The indicating circuit 30 is a circuit able to divide an input electrical signal supplied thereto into a D.C. component and an A.C. component and to separately indicate them.

As shown in FIG. 4, the indicating circuit 30 is connected to the strain sensitive element 21a through the connector 27 of the top portion of the case member 25.

The connector 27 for the indicating circuit 30 includes first, second, third, fourth and fifth input terminals 31a, 31b, 13c, 31d, 31e, respectively, and the first input terminal 31a is grounded and the fourth input terminal 31d is connected to a voltage-adjusting-variable resistor 32. The voltage adjusting vairable resistor 32 adjusts a voltage to be supplied to a given voltage level, with one terminal 32a thereof being connected to the fourth input terminal 31d, the other terminal 32b thereof being connected to a power source 33. The power source 33 is a stable D.C. power source and rectifies A.C. 100 V into a D.C. voltage which has been compensated for a variation in power source. A terminal 33a of the power source 33 is connected to the other terminal 32b of the voltage adjusting variable resistor 32.

A voltage-balance-adjusting-slide resistor 34 is connected between the second input terminal 31b and the third input terminal 31c, while the slide terminal 34a of the voltage-balance-adjusting-slide resistor 34 is connected to a temperature compensating circuit 35.

The temperature compensating circuit 35 varies its resistance with a change in temperature, thereby adjusting a current passing therethrough. The circuit 35 includes a fixed resistor 35a and a thermister 35b which are connected in series. The circuit 35 compensates for the influence on the strain sensitive elements 21a based on expansion and contraction of the silicon resilient material disposed in the pressure transmitting cell in the aforesaid pressure-electric transducing portion 20 due to a temperature change, as well as the lowering in sensitivity of the strain sensitive element itself. An input terminal 35c of the temperature compensating circuit 35 is connected to a slide terminal 34a of the voltage-balance-adjusting-slide resistor 34, while an output terminal 35d thereof is connected to a differential amplifier 36.

The differential amplifier 36 includes first and second input terminals 36a, 36b, and subtracts voltage signals delivered from the first and second input terminals 36a, 36b one from the other, followed by amplification of a difference voltage subtracted at a given amplification degree for supplying the voltage. A first input terminal 36a of the differential amplifier 36 is connected to an output terminal 35d of the temperature compensating circuit 35, while a second input terminal 36b is connected to the fifth input terminal 31e. An output terminal 36c of the differential amplifier 36 is connected to a variable capacitor 37 and a smoothing circuit 38 connected to the variable capacitor 37, respectively.

The variable capacitor 37 cuts off a D.C. component in the difference signal from the differential amplifier 36, and allows only an A.C. component to pass therethrough, as well as to adjust a time constant by the cooperation of a resistor in a recorder 39 which will be described later. To this end, an input terminal 37a of the variable capacitor 37 is connected to an output terminal 36c of the preceding stage differential amplifier 36, while an output terminal 37b thereof is connected to the recorder 39.

The recorder 39 is referred to as a pen-writing recorder, which analogically follows a time variation according to a voltage signal being fed from the capacitor 37, thereby recording signals on a recording sheet. In this respect, an input terminal of the recorder 39 is connected to an output terminal 37b of the variable capacitor 37.

The smoothing circuit 38 smoothens an A.C. component into a D.C. component, and includes a choke coil 38a, and two capacitors 38b, 38c. An input terminal 38d of the smoothing circuit 38 is connected to an output terminal 36c of the differential amplifier 36, while an output terminal 38e is connected to the next stage D.C. voltmeter 301.

The D.C. voltmeter 301 indicates the D.C. voltage from the smoothing circuit 38 analogically, while a linear scale is graduated on an indicating portion of the D.C. voltmeter 301 in terms of a pressure, and is adapted to incorporate a range-changeover switch adapted to enlarge a range of graduations, as required. An input terminal 301a of the D.C. voltmeter 301 is connected to an output terminal 38e of the smoothing circuit 38. Respective output terminals of the recorder 39 and D.C. voltmeter 301 are grounded.

Figure 5:
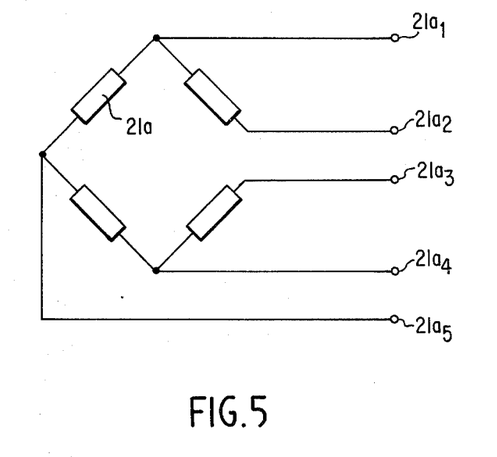

The first, second, third, fourth and fifth input terminals 31a, 31b, 31c, 31d, and 31e, respectively, of the indicating circuit 30 are connected to first, second, third, fourth and fifth output terminals 21a1, 21a2, 21a3, 21a4, 21a5, respectively, of a bridge circuit which consists of strain sensitive elements 21a positioned on the pressure-electric transducing portion 20, as shown in FIG. 5.

A description will now be given of the operation of an intracranial pressure transducer according to the first embodiment of the invention.

Figure 6:
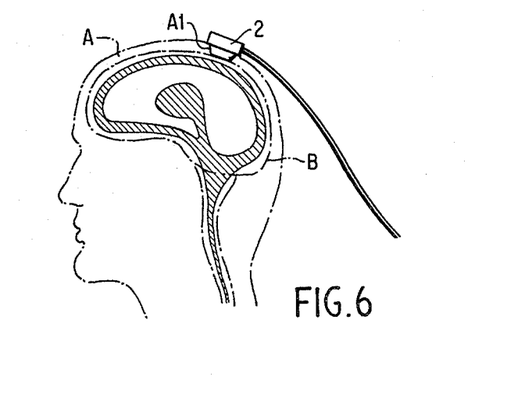
FIG. 6 is a view illustrative of the use of the intracranial pressure transducer according to the aforesaid embodiments wherein an intracranial pressure transducer is placed into a hole in a skull.

Before detecting an internal pressure and a pulse pressure in a skull by means of an intracranial pressure transducer according to the invention, a drill hole A1 for inserting an adapter plug 10 is provided in a measured position of a skull A of a head, with the center axis of the hole A1 being in alignment with the center point of the head.

Since the thickness of the skull A varies with a patient to be measured, the thickness of a skull is measured. Then, an adapter plug 10 suited for the thickness measured is selected, and then the adapter plug 10 is located in the hole A1, and then an embossed cross-tip of a tool is fitted in the cross-wise channels 12a and then rotated, so that the adapter plug 10 is threadedly fixed to the skull A, with the tip 13 of the adapter plug 10 reaching the dura B under the skull A. Thereafter, the tip, pressure receiving layer 25e of the pressure-electric transducing portion 20, is inserted into the through-hole or inner hole 11 in the adapter plug 10 in opposed contact relation to the dura B under the skull A. On the other hand, bolt holes 25g in the case member 25 are opposed to the blind screw holes 12b in the adapter plug 10, so that both the pressure-electric transducing portion 20 and the adapter plug 10 are fastened together by means of bolts 25h. In this respect, the tip 25d of the pressure electric transducing portion 20 protrudes a predetermined distance from the tip 13 of the adapter plug 10, so that the dura B under the skull A is depressed to an extent corresponding thereto. The above protruding portion of the tip 25d brings tension of the dura B and a pressing force into equilibrium. In other words, the tip surface of the pressure layer 25e presses the dura to be coplanar, so that internal pressure (i.e., intracranial pressure) and external pressure (i.e., internal pressure of the receiving layer 25e) against the dura are equal by cancelling tension forces of the dura as a Coplanar method, and this is a compensating means which allows an accurate measurement of an internal pressures in the skull over a wide range convering a low internal pressure to a high internal pressure.

As a result, an internal pressure and a pulse pressure in the skull is accurately transmitted through the medium of the dura B under the skull A to the pressure receiving layer 25e disposed at the tip 25d of the pressure-electric transducing portion 20 so that an internal pressure and pulse pressure thus transmitted are then transmitted to the strain sensitive elements 21a disposed on the strain sensitive member 21 in the pressure-electric transducer 24, and transduced into an electrical signal. The electrical signal is fed to the indicating circuit 30 and indicated in the form of a D.C. component and an A.C. component, separately.

Meanwhile, a pressure in the pressure electric transducing portion 20, which is forced against the dura B is indicated as a D.C. component, while a pulse pressure self is indicated as an A.C. component.

The strain sensitive elements 21a are adapted to convert a pressure into an electric signal and the strain sensitive member 21 are integrally provided in the pressure-electric transducer 24 disposed in the pressure-electric transducing portion 20 so that the transducer 24 can be extremely reduced in size and thickness, and provide high sensitivity. As a result, even a small pressure variation can be accurately transduced into an electric signal proportional to the aforesaid pressure variation.

In addition, the pressure-electric transducer 24 comprising the strain sensing member 21 and the first and second supporting members 22, 23 supporting the member 21 is charged in the case member 25. The pressure-electric transducer 24 is provided with a pressure transmitting portion or the pressure receiving layer 25e having a desired resiliency and a reduced thickness at the lower portion thereof. The pressure receiving layer 25e is provided with a given pressure receiving surface which is to be in contact with a dura under the skull in order to receive an internal pressure and a pulse pressure in the skull and to transmit such pressures to the strain sensing member 21 having strain sensitive elements 21a through the pressure receiving layer 25e. Accordingly, if an intracranial pressure is applied to the pressure receiving layer 25e through the dura, then the pressure is transmitted to the pressure transmitting portion or the pressure receiving layer 25e as an internal pressure. Meanwhile, the peripheral edge of the pressure transmitting portion is surrounded by the annular leg portion 25b, first and second supporting members 22, 23 in the pressure electric transducer 24, and dura B under the skull A, so that free expansion is restricted to the minimum i.e., the dura is maintained to be coplanar. As a result, the internal pressure of the layer 25e is equal to the intracranial pressure of a Coplanar method, and the internal pressure is applied to the strain sensing member 21 having the strain sensitive element 21a thereon, without being lowered or dampened, so that high measuring accuracy can be achieved by the attainment of practical and convenient Coplanar method according to the present invention.

More particularly, when the pressure receiving layer 25e is set to a measuring position or hole A1 in the skull, the dura B under the hole A1 has a curvature which protrudes outwardly, in proportion to an internal pressure in a skull. When a pressure receiving surface according to a diaphragm portion, of an intracranial pressure transducer is forced directly against the above curvature of the dura B then there results a point contact therebetween, so that a concentrated stress is applied to strain-sensitive elements of the diaphragm directly. As a result, there is developed an abnormally high output voltage. However, in the present invention the pressure receiving layer 25e having a given thickness and resiliency is provided on the strain sensitive element 21a, thereby neutralizing a concentrated stress at the time of contact with the dura B.

Since the strain sensing element 21a disposed on the strain sensing member 21 adapted to convert a pressure into an electrical signal is extremely sensitive to a temperature change, in such case the strain sensitive elements 21a at room temperature are brought into contact with an organism at about 37° C. and the strain sensitive elements 21a tend to drift due to a transient temperature change. However, in the present invention the pressure receiving layer 25e will not directly transmit a temperature change to the strain sensitive elements 21a by temporarily suppressing a temperature rise.

Since the pressure receiving layer 25e is made of a silicon resin, a patient to be measured does not experience an uncomfortable feeling, and thus a mental condition of a patient will not be irritated but rather be maintained in a stable condition.

In addition, even if the pressure receiving layer 25e at the tip 25d of the pressure-electric transducing portion 20 is only slightly forced against the dura B corresponding to a position to be measured, an internal pressure and a pulse pressure in the skull may be measured to some extent. However, the pressure-electric transducing portion 20 can hardly be manually held in a stable condition, so that an internal pressure and a pulse pressure can not be detected accurately.

According to the present invention, the pressure electric transducing portion 20 is secured to the adapter plug 10, so that the pressure electric transducing portion 20 can be held in a desired position in a stable manner, even if a patient is unfavorably moved to some extent. The pressure-electric transducing portion 20 can be thus held in position for a long period of time. In addition, a minute variation in the pulse pressure under a consistent pressure on the dura B can be measured for a long period of time.

Other than the measurement of an internal pressure and a pulse pressure in a skull according to the intracranial pressure transducer of the present invention for a relatively short period of time, there arises cases where a measuring monitor is required to be used for a long period of time before and after an operation. In this first embodiment, an annular depending portion 25b of a cylindrical shape internally of the case member 25 is provided with the circumferentially stepped portion 25i. Accordingly, when the pressure electric transducing portion 20 is secured to the adapter plug 10, there is provided a clearance 25j between the adapter plug 10 and the annular depending portion 25b of the case member 25 in the pressure electric transducing portion 20, and then the clearance 25j is communicated via cross grooves 12a provided on the top surface of the adapter plug 10 to the atmosphere, so that even if a body fluid and blood is exuded during the operation, blood can be discharged through the clearances 25j and the grooves 12a to the exterior of the transducer. In other words, blood does not become disposed between the pressure receiving layer 25e in the pressure-electric transducing portion 20 and the dura B, thus ensuring accurate measurement of an internal pressure and a pulse pressure in a skull.

Meanwhile, the connector 27 is led in the longitudinal direction of the pressure-electric transducing portion 20. This is because if the connector 27 is led therefrom in the vertical direction from the hole A1 in the skull A, i.e. in the width direction of the pressure electric transducing portion 20, the connector 27 tends to fall on its side. In other words, the connector 27 can not be held in a stable condition. This leads to a variation in a force to press the pressure receiving layer 25e in the pressure electric transducing portion 20, thereby causing an error in measurement. In addition, an unstable condition of the connector 27 can possibly lead to damage on the dura. In the worst possible case, cerebromeningitis is caused by infection from the exterior. The aforesaid arrangement of the connector 27 ensures stable measurement for a long period of time.

In this first embodiment, the adapter plug 10 and case member 25 are made of stainless steel, thereby presenting high strength and high acid- resistant and alkali-resistant properties so that the intracranial pressure transducer of the first embodiment according to the present invention has a high resistance to a body fluid such as blood.

Thus, a pressure and a pulse pressure within the skull A can be received by the pressure receiving layer 25e of the pressure-electric transducing portion 20 as the internal pressure, and then converted into an electrical signal according to a piezoresistive effect of the strain sensitive elements 21a on the semiconductor strain sensing member 21. Thereafter, an electrical signal is delivered via lead pins 23c and connector 27 to the indicating circuit 30.

The intracranial pressure transducer of the present invention including the pressure-electric transducing portion 20 and adapter plug 10 in combination with the circuit as shown in FIG. 4 provides the following advantage, and hence greatly contributes to a clinical field of medicine.

Hitherto, an output signal of the intracranial pressure transducer as shown in FIG. 3 may be indicated in the form of a pattern of a pulse pressure on an oscillograph and the pattern may then be observed. However, in prior art circuits an output signal of the intracranial pressure transducer is provided as a combination of a signal representing a variation in internal pressure in the pressure transmitting portion in the pressure-electric transducing portion 20 due to a variation in a force to press the dura, with another signal representing a variation in pulse pressure itself. As a result, even if a variation in pulse pressure relative to a force to press the dura is desired to be detected, the prior art transducer fails to meet this requirement.

According to the pressure-electric transducing portion 20 of the invention, a D.C. voltage which has been adjusted by the voltage adjusting resistor 32 is supplied from the stable electric power source 33 in the indicating circuit 30 to a bridge circuit including the strain sensitive elements 21a in the pressure electric transducing portion 20.

A variation in internal pressure and pulse pressure in the skull can be converted into an electric signal according to the piezoresistive effect of the strain-sensitive elements 21a in the pressure-electric transducing portion 20 and then the electric signal is delivered to the indicating circuit 30. One input signal from the bridge circuit consisting of strain sensitive elements 21a is supplied to the temperature compensating circuit 35 in the indicating circuit 30 through the voltage-balance-adjusting-slide resistor 34.

The temperature compensating circuit 35 compensates for the influence on the strain sensitive elements 21a of the expansion and contraction of a silicon resilient material (pressure receiving layer 25e) disposed on the pressure electric transducer 24 due to a temperature change, as well as for the lowering in sensitivity of the strain sensitive elements 21a themselves by varying the resistance variation corresponding to a temperature change. Accordingly, a signal compensated for temperature change is fed to one input terminal 36a of the differential amplifier 36 connected to the temperature compensating circuit 35. The other signal from the bridge circuit is supplied to the other input terminal 36b of the differential amplifier 36, as is.

Figure 7:
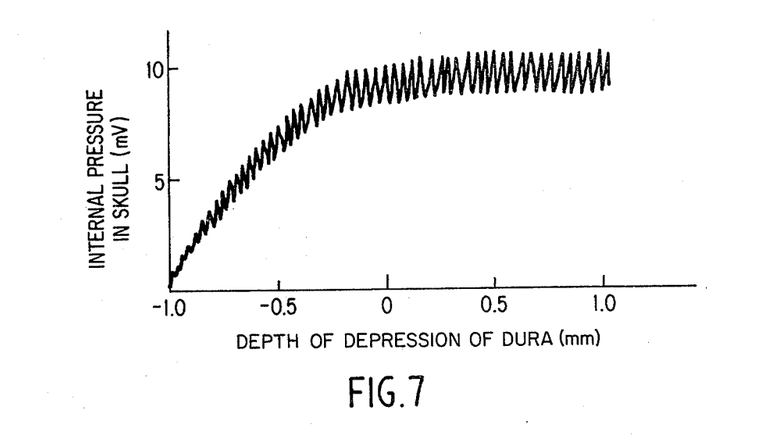
FIGS. 7, 7A, 7B are graphical presentations showing internal pressures and pulse pressures in the skull of a human body, which have been detected by the intracranial pressure transducer according to the aforesaid embodiments.

The differential amplifier 36 subtracts voltage signals supplied to the first and second input terminals 36a, 36b one from the other, and then amplifies this difference voltage signal at a given amplification degree, so that the difference voltage signal including D.C. and A.C. components as shown in FIG. 7, subtracted one from the other and amplified at a given amplification degree, is supplied to the variable capacitor 37 and smoothing circuit 38, which are connected to the differential amplifier, respectively.

Figure 7A:
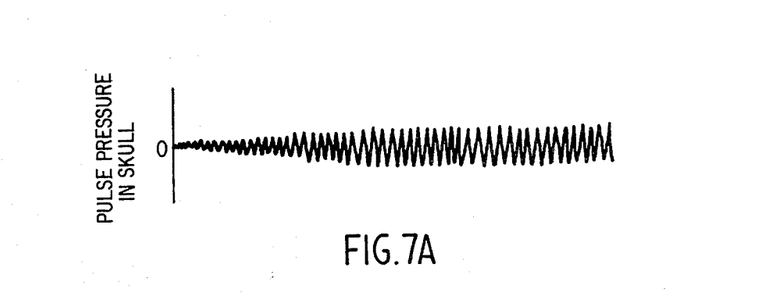

The variable capacitor 37 cuts off a D.C. component and allows an A.C. component to pass therethrough, so that the D.C. component included in an output signal of the differential amplifier 36 are cut off, while the A.C. component alone as shown in FIG. 7A is supplied to the recorder 39 connected to the variable capacitor 37.

The recorder 39 records signals from the variable capacitor 37 on a recording sheet, following a change in time. In other words, the recorder 39 records the signals of A.C. component from the variable capacitor 37, i.e. pulse pressure signals of A.C. component detected by the pressure receiving layer 25e of the pressure-electric transducing portion 20, which layer is being pressed against the dura B under the skull A of a body to be measured.

Figure 7B:
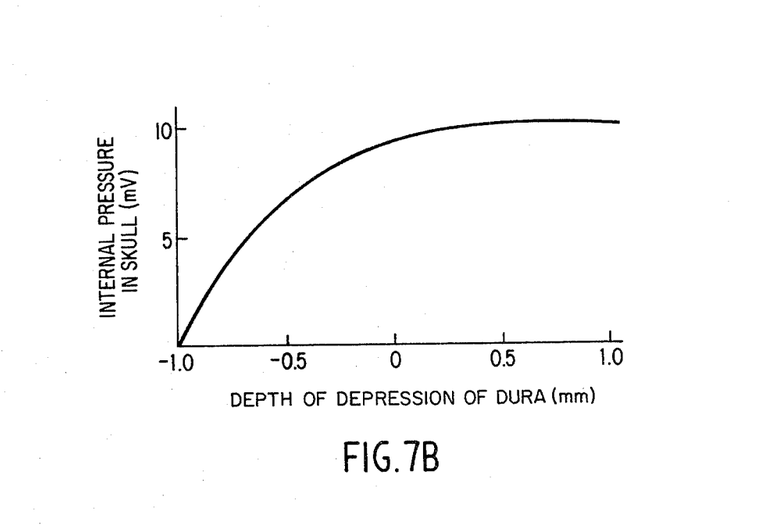

The smoothing circuit 38 smoothens the A.C. components into D.C. components so that A.C. components included in an output signal from differential amplifier 36 are all smoothened into D.C. components as shown in FIG. 7B which are then supplied to the voltmeter 301 connected to the smoothing circuit 38.

The D.C. voltmeter 301 analogically indicates a D.C. voltage signal being supplied from the smoothing circuit 38 thereto, while a linear scale is graduated in an indicating portion of the D.C. voltmeter 301 in terms of a pressure. As a result, the difference signal respresenting the D.C. component from the smoothing circuit 38, i.e., a pressure signal developed by pressing the pressure receiving membrane layer 25e of the pressure electric transducing portion 20 against the dura B under the skull A (i.e. an internal pressure in the skull), can be analogically indicated thereon. In other words, a force to press the pressure receiving membrane layer 25e of the pressure electric transducing portion 20 against the dura B of a body to be measured can be detected in terms of a variation in analogical indication.

FIG. 7 shows a clinical example wherein variations in an internal pressure and pulse pressure in the skull are detected by means of the circuit shown in FIG. 4 of an intracranial pressure transducer of the first embodiment according to the present invention.

In FIG. 7, the abscissa represents a depth of depressing a dura under the skull by the pressure electric transducing portion 20 in the intracranial pressure transducer, while the ordinate represents an intracranial pressure under the skull. Thus, a variation in internal pressure and pulse pressure under the skull are indicated with pen recorder. FIG. 7A represents A.C. components included in an output of the pressure electric transducing portion 20 while FIG. 7B represents D.C. components included in the above output.

In this clinical example, a position just under the skull is taken as a reference point which shows 0 (mm) of depth of depression of a dura under the skull as shown in FIG. 7. When the dura under the skull is depressed by the tip 25b of the pressure electric transducing portion 20 to a depth of 0.5 to 1.0 mm from the reference point, internal pressure under the skull maintains a constant pressure, and also a pulse pressure can be detected clearly.

The depth at which the clearest detection can be obtained depends on a body to be measured. Accordingly, when the intracranial pressure transducer of the first embodiment according to the present invention is used, a depth of the dura to be depressed by the pressure electric transducing portion 20 is determined to an optimum position to accurately detect an internal pressure and a pulse pressure under the skull and the detection can be continued under the above condition for a long period of time.

In this manner, the intracranial pressure transducer according to the first embodiment in the present invention can measure an internal pressure and a pulse pressure under the skull, without damaging the dura present under the skull of a body to be measured. This inracranail pressure transducer is quite safe for use and well adapted for use not only for a long period of time but also for a short period of time, thus presenting many advantages in the fields of cerebro-surgery and cerebro and neuro-surgery.

However, the intracranial pressure transducer according to the first embodiment can still be less than satisfactory upon measurement from the viewpoint of its operation in some instances. In other words, when the pressure-electric transducing portion 20 is secured to the adapter plug 10, an extent of the pressure electric transducing portion 20 which protrudes from the tip of the adapter plug 10 is primarily determined.

The thickness and resiliency of the dura which are associated with measurement vary depending on the age, sex and personal difference of patients to be measured. As a result, when the intracranial pressure transducer according to the first embodiment is desired to be set to an optimum condition, according to patients to be measured, the pressure electric transducing portion 20 should be removed from the adapter plug 10 and then a spacer having a suitable thickness is inserted therebetween, for adjusting a protruding extent of the pressure electric transducing portion 20. Otherwise an adapter plug 10 suited for a body to be measured should be selected. In either case, simple adjustment can not be achieved.

Figure 8:
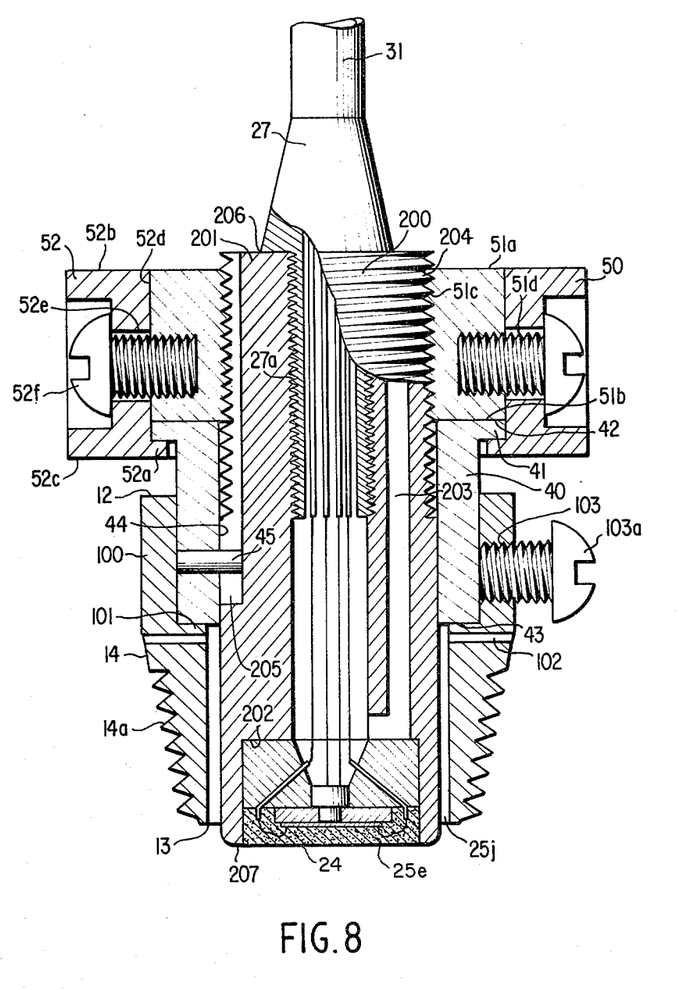
FIG. 8 is a cross-sectional view of the intracranial pressure transducer according to the second embodiment of the invention.

Difficulty in the aforesaid adjustment can be overcome according to the intracranial pressure transducer according to a second embodiment in the present invention, in which an intermediate ring 40 and a rotatable member 50 are interposed between the adapter plug 10 and the pressure electric transducing portion 20 such that the pressure electric transducing portion 20 can slide in a vertical direction to an extent depending on the thickness of a skull and resiliency of a dura of a body to be measured.

Description will now be turned to the intracranial pressure transducer according to the second embodiment in the present invention with reference to FIG. 8. The same parts as in the first embodiment are designated with the same reference numerals as those given in the first embodiment. The detailed descriptions thereto will be omitted in this second embodiment.

The intracranial pressure transducer according to the second embodiment includes an adapter plug 100 as a part of an adapter in the casing, which is to be threadedly fixed in a hole in the skull of a patient, a pressure-electric transducing portion 200 adapted to be secured to the adapter plug 100 and for detecting an internal pressure and a pulse pressure in the skull in the form of an electrical signal, an intermediate ring 40 as a part of the adapter in the casing, which is mounted between the adapter plug 100 and the pressure electric transducing portion 200 and allowing vertical sliding of the pressure electric transducing portion 200 alone; a rotatable member 50 as a part of the adapter in the casing, which is rotatable on the intermediate ring 40 and housing the pressure-electric transducing portion 200 therein, so that the pressure-electric transducing portion 200 can be moved in the vertical direction due to the rotation of the rotatable member 50; and an indicating circuit 30 for indicating an output signal of the pressure-electric transducing portion 200. The casing in this second embodiment comprises an adapter comprising an adapter plug 100, intermediate member 40 and rotatable member 50; and a case member comprising a case member 201.

The adapter plug 100 to be threadedly fixed in a hole in the skull of a body to be measured is made of stainless steel, and its shape is similar to that of the adapter plug 10 in the intracranial pressure transducer according to the first embodiment. However, a circumferentially stepped portion 101 is provided in the wall of an internal hole in the adapter plug 100 for mounting the intermediate ring 40 thereon.

Meanwhile, the top surface 12 of the adapter plug 100 is flat, while the outer peripheral surface of the adapter plug 100 is tapered as shown at numeral 14 from the top surface 12 of the plug 100 towards the buttom surface 13 as in the adapter plug 10 in the first embodiment. In addition, threads 14a are formed on the tapered surface of the plug 100 to be threadedly secured to a skull of a head of a patient to be measured.

A circumferentially stepped portion 101 is formed on the wall of an internal hole in the adapter plug 100 in concentric relation to the hole. An internal hole above the stepped portion 101 and another internal hole under the stepped portion 101 are both of a cylindrical shape and coaxial with each other. In this respect, the inner diameter of the internal hole under the stepped portion 101 is larger than the outer diameter of a case member 201 as a case member in the casing for enclosing the pressure-electric transducing portion 200 to be described later, so that when the pressure electric transducing portion 200 is mounted in the adapter plug 100, there may be provided a clearance 25j of a cylindrical form between the outer peripheral surface of the casing 201 in the pressure electric transducing portion 200 and the inner peripheral surface of the adapter plug 100. The clearance 25j is communicated with side through-holes 102 extending through the wall of the adapter plug 100 between the exterior and the interior of the adapter plug 100. The side through-holes 102 are disposed at an angularly equal space in the side wall of the adapter plug 100.

The inner diameter of the upper internal hole above the stepped portion 101 is larger than the inner diameter of the lower internal hole under the stepped portion 101, and substantially equal to the outer diameter of the intermediate ring 40 to be described later. Screw holes 103 are provided in the side wall of the upper internal hole of the plug 100 at an equal angular space in a manner to extend from the outer peripheral surface of the inner peripheral surface of the wall of the adapter ring 100. Screw 103a is threaded into the screw holes 103, so that the intermediate ring 40 can be seated on the stepped portion 101 inwardly of the adapter plug 100 and locked in position.

Meanwhile, the intermediate ring 40 fitted in the adapter ring 100 is made of stainless steel, and formed with an upper flange portion 41 protruding outwardly. The top and bottom surfaces 42, 43 of the ring 40 are flat, while the diameter of the outer peripheral surface of the intermediate ring is substantially the same as the diameter of the upper internal hole above the adapter ring 100. In addition, a through-hole 44 extends through the top surface 42 to the bottom surface 43 along the axis of the ring 40, and the through-hole 44 is concentric with the intermediate ring 40.

A drive pin 45 is provided in the intermediate ring 40 in a manner so as to protrude from the inner wall of the ring 40 inwardly. The diameter of the through-hole 44 is slightly larger than the outer diameter of the case member 201 for the pressure-electric transducing portion 200 to be described later, thereby allowing the vertical sliding of the pressure-electric transducing portion 200.

The flange portion 41 flush with the top surface 42 of the intermediate ring 40 is of an annular shape, and protrudes outwardly for supporting the rotatable member 50 thereon.

The rotatable member 50 supported by the intermediate ring 40 is made of stainless steel, and consists of first and second rotatable members 51, 52. The top surface 51a and bottom surface 51b of the first of the first rotatable member 51 are flat, and has a through-hole 51c extending from the top surface 51a to the bottom surface 51b in concentric relation to the member 51. The inner wall of the through-hole 51c is threaded. The inner diameter of the through hole 51c is substantially the same as the diameter of the outer peripheral wall of the casing 201 in the pressure-electric transducing portion 200 to be described later, so that the pressure-electric transducing portion 200 may be threaded into the through hole 51c.

Screw holes 51d of a blind form are provided in the wall of the rotatable member 51 at an equal angular spaces along the circumference thereof, while the diameter of the outer peripheral wall of the member 51 is substantially the same as the outer diameter of the flange portion 41 of the intermediate ring 40, so that the rotatable member 51 may be threaded into the second rotatable member 52.

The rotatable member 52 which is threaded into the first rotatable member 51 is provided with a flange portion 52a protruding from the lower inner peripheral portion thereof, and the top surface 52b and bottom surface 52c thereof are flat. The axial thickness of the second rotatable member 52 is greater than that of the first rotatable member 51. A through-hole 52d extends between the top and bottom surfaces 52b, 52c in concentric relation to the member 51. In addition, the inner diameter of the through-hole 52d is substantially the same as that of the outer peripheral wall of the rotatable member 51.

Bolt holes 52e are provided in the outer peripheral wall of the rotatable member 52 at an equal angular space along the circumference thereof. The bolt holes 52e register with blind type screw holes 51d provided in the wall of the first rotatable member 51 at an equal angular space along the circumference thereof. This permits the insertion of bolts 52f through the holes 51d, 52e, so that the first and second rotatable members 51, 52 can be fastened together.

A flange portion 52a extends inwardly from the lower end portion 52c of the rotatable member 52 and is of an annular shape, while the inner diameter of the flange portion 52a is slightly smaller than the outer diameter of the flange portion 41 of the intermediate ring 40, thereby allowing an interference fit therebetween. The first and second rotatable members 51, 52 can rotate jointly, while sliding on the top surface 42 of the intermediate ring 40 and being supported on the intermediate ring 40.

Meanwhile, the pressure-electric transducing portion 200 is mounted in the rotatable member 50 and intermediate ring 40. The pressure-electric transducing portion 200 converts an external pressure based on the intracranial pressure and pulse pressure under the skull into an electric signal, and consists of a case member 201 and a pressure-electric transducer 24.

The case member 201 is of a cylindrical form and made of stainless steel, having a length greater than the axial length of the intermediate ring 40 and rotatable member 50. A circumferentially stepped portion 202 is provided in the inner peripheral wall of an internal hole in the case member 201 in concentric relation to the casing, with an internal hole above the stepped portion 202 and another internal hole under the stepped portion 202 being both of a cylindrical shape in coaxial relation. The inner diameter of the upper internal hole above the stepped portion 202 is smaller than the inner diameter of the lower internal hole under the stepped portion 202, whereby the pressure-electric transducer 24 is placed in the lower internal hole under the stepped portion 202 in a stable manner. Meanwhile, description will be omitted herein of the pressure-electric transducer 24 which is similar to the pressure-electric transducer 24 according to the first embodiment in the present invention.

A communicating hole 203 extends through the wall of the case member 201 between the outer peripheral wall of the case member 201 and the wall of the upper internal hole in parallel with the axis of the case member 201. The communicating hole 203 is open from one end thereof, and is also open into the upper internal hole at the other end, so that atmospheric air may be introduced through the communicating hole 203 internally of the case member 201. Threads 204 are formed on the outer peripheral wall of the case member 201 in a range covering from the top surface to the middle point of the axial length of the casing, while a single run of a groove 205 is provided in the outer peripheral surface of the case member 201 in parallel with the axis thereof in a range from the top surface 206 to the neighborhood of the bottom surface 207. When the case member 201 is fitted in the intermediate ring 40 and rotatable member 50, a driven pin 45 formed on the intermediate ring 40 can be fitted in the groove 205 provided in the casing 201, while the threads 204 on the case member 201 engage the screw hole 51c provided in the rotatable member 50, so that the rotation of the pressure-electric transducing portion 200 is prevented, while the vertical displacement of the pressure-electric transducing portion 200 alone is allowed.

A connector 27 is threaded as at 27a in the upper thermal hole through the top surface 206 of the case member 201. In this respect, the terminals of the connector 27 inside the case member 201 are connected to the lead pins 23c of the pressure-electric transducer 24, while the terminals of the connector 27 outside the case member 201 are connected to plugs 31 in the indicating circuit 30 for the intracranial pressure transducer as shown in the first embodiment of the present invention. Thus, an electrical signal can be derived from the connector 27.

When an internal pressure and a pulse pressure under the skull are detected by an intracranial pressure transducer according to the second embodiment in the present invention, as has been described earlier in the first embodiment, careful attention should be paid to drilling into the skull in a position to be measured, with the center axis of the drill hole being in alignment with the center of the head.

Then the adapter plug 100 is brought to a drill hole thus prepared, and fixed therein, while being rotated by means of a tool. The adapter plug 100 is fixedly threaded into the drill hole in a position where the tip of the adapter plug 100 reaches a dura under a skull.

In this respect, as in the first embodiment, the type of the adapter plug 100 is selected depending on the thickness of the skull of a patient to be measured, as has been described earlier. However, in the second embodiment, the adapter plug 100 suited for the thickness measured should not necessarily be so selected, since the intracranial pressure transducer according to this second embodiment are constructed as follows. Namely, the pressure-electric transducing portion 200 is placed in the through-hole 11 in the adapter plug 100 in a slidable manner only in the vertical direction by means of the intermediate ring 40, and yet threaded into the rotatable member 50. Thus, the pressure-electric transducing portion 200 is inserted in the through-hole 11 in the adapter plug 100, with the tip portion of pressure receiving layer 25e of the portion 200 facing the dura under a skull in a position to be measured, after which the portion 200 is locked in position by means of screws 103 threaded in the screw holes 103 provided in the wall of the adapter ring 100.

Then, the rotatable member 50 is rotated so as to cause the pressure-electric transducing portion 200 to slide in the vertical direction, in a manner that the pressure receiving layer 25e of the pressure-electric transducing portion 200 protrudes from the end of the adapter ring 100, thereby depressing a dura under a skull for balancing a tension of the dura and a force to press the dura into equilibrium.

In this manner, an internal pressure and a pulse pressure under the skull can be accurately transmitted through the medium of the dura under the skull to the pressure receiving layer 25e at the tip of the pressure-electric transducing portion 200, and then the internal pressure and pulse pressure thus transmitted are also transmitted to the strain sensitive elements 21a on the strain sensing member 21 in the pressure-electric transducing portion 200 so as to be converted into an electrical signal, which in turn is supplied to the indicating circuit 30 via the connector 27. The electrical signal supplied to the indicating circuit 30 is separated into a D.C. component and an A.C. component, while the D.C. component represents an internal pressure, and the A.C. component represents a pulse pressure.

As is apparent from the foregoing, the intracranial pressure transducer according to the second embodiment allows clearest observation or detection and simple adjustment therefor, corresponding to the thickness of a skull and the resiliency of the dura. The aforesaid thickness and resiliency vary depending on the age, sex and personal difference of patients. In addition, the aforesaid observation or detection can be carried out for a long period of time, and a variation in pulse pressure of a patient due to a variation in a force pressing the dura can be detected jointly with a detection of an internal pressure under the skull.

While description has been given thus far of the specific embodiments of the invention, it should be understood that the present invention is by no means limited to these embodiments, but may be modified in various forms.

The casing has axial passages for excreting a body fluid from the body and blood between the skull and dura, so as to prevent the filling and the coagulation of the body fluid and blood between the skull and dura, and attain the accurate measurement of the intracranial pressure.

The strain sensing element of the present invention is selected one from the group consisting of the diffused strain gauge formed on the surface of said diaphragm by the diffused method, a foil gauge bonded on the surface of said diaphragm, and differential transformer means in which a core connected to said diaphragm is movable in the axial direction within a pair of coil.

The adapter is rotatably engaged to said case member, so as to insert said case member in the axial direction within the skull of the body by rotating said adapter without rotating said case member. For instance, in the first embodiment, the adapter plug 10 and the case member 25 for the pressure-electric transducing portion 20 are provided separately. However, these members may be provided integrally with each other.

In addition, the adapter plug 10 and casing 25 in the first embodiment as well as the adapter ring 100, intermediate ring 40, rotatable member 50 and the case member 201 in the second embodiment are made of stainless steel. However, the present invention should not necessarily be limited to the above material. These members may be made of a material which resists corrosion due to blood, for instance, durolumin, synthetic resin and the like which are resistant to acid and alkali.

Still furthermore, a semiconductor pressure-electric transducing element is used as the transducer 24 in the pressure-electric transducing portion 200 in the intracranial pressure transducer according to the first and second embodiments. However, the present invention should not necessarily be limited to these instances. A differential transformer, foil gage and the like may be used in place of these components.

Yet furthermore, the intracranial pressure transducers according to the first and second embodiments are used for the measurement of an internal pressure and a pulse pressure in the skull of a human body. However, this may be used for animals such as dog, cat and the like.

In short, the intracranial pressure transducer according to the present invention includes an adapter portion threadedly fixed to the skull of a body to be measured, a pressure-electric transducing portion adapted to be inserted into the adapter portion, with the pressure receiving layer at the tip thereof being in press contact with the dura under a skull of a body to be measured for measuring an internal pressure and a pulse pressure in the skull of a body to be measured, and an indicating circuit for indicating an output signal of the pressure-electric transducing portion. Thus, since the adapter portion is threadedly fixed to the skull of a body to be measured, and the pressure receiving layer at the top of the pressure-electric transducing portion thus inserted and fixed is brought into pressing contact with the dural of a body to be measured, the measuring condition can be maintained in a stable condition. In addition, an internal pressure and a pulse pressure supplied from a body to the pressure receiving layer at the top of the transducing portion may be positively accurately detected by the pressure electric transducing portion so as to be converted into an electrical signal. The electrical signal may be indicated by a suitable indicating means, thereby detecting an internal pressure and a pulse pressure under the skull, thus contributing greatly to the field of clinical medicine.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An intracranial pressure transducer which comprises:

a casing comprising an annular member having a threaded part on a radially outer wall thereof for fitting and securing to a skull of a body, a pressure-electric transducing portion comprising a supporting member which is inserted within a radially inner wall of said casing and is tightly fixed to a predetermined first portion of said casing at a first portion of said supporting member, and which has a hole of predetermined diameter, a thin strain sensing member 21 having a first surface bonded to a second surface of said supporting member 22 having said hole in order to close said hole, at least one strain sensitive element having two ends for converting the strain of said strain sensing member into an electrical signal provided at a strain sensing region, which region corresponds to said hole of said supporting member, on said thin strain sensing member, lead wires connected to said strain sensitive element through electrodes provided at both ends of said strain sensitive element and a receiving connector provided at an upper portion of said casing, and a pressure receiving layer adapted to be in contact with a dura under the skull and comprising resiliently compressible material for receiving an intracranial pressure under the dura as an internal pressure thereof which fills up a concave portion formed by a radially inner wall of a second portion of said casing, a portion of said second surface of said supporting member, and said second surface of said thin strain sensing member, and an indicating circuit, for indicating the intracranial pressure, in response to an output of said strain sensitive element, comprising an amplifier circuit connected to said lead wires within said pressure-electric transducing portion through connector means for engaging with said receiving connector, and indicating means connected thereto, whereby the intracranial pressure of a cerebrospinal fluid is converted to the internal pressure of the pressure receiving layer with the intracranial pressure transducer by means of a Coplanar method which maintains the dura to be coplanar by the depression of the pressure receiving layer of the transducer against the dura; the internal pressure of the pressure receiving layer being applied to the strain sensing member; the electrical signal being supplied by the strain sensitive element in response to the internal pressure of the pressure receiving layer; and the intracranial pressure being indicated on the indicating means.

2. An intracranial pressure transducer according to claim 1, wherein:

said casing comprises an adapter including said annular member and a case member which encloses said pressure-electric transducing portion and is inserted within a radially inner wall of said adapter and is fixed to said adapter at a first portion thereof in order to provide that a second portion of said case member protrudes from a second portion of said adapter a predetermined length.

3. An intracranial pressure transducer according to claim 2, wherein:

said adapter is rotatably engaged to said case member, such that said case member is inserted in an axial direction within the skull of the body by rotating said adapter without rotating said case member.

4. An intracranial pressure transducer according to claim 2, wherein:

said adapter comprises a first annular member having a threaded part on a radially outer wall thereof for fitting and securing to the skull of the body, a second annular member, having a fixing means for preventing the rotation of said case member by engaging it with a groove formed on a radially outer wall of said case member, which is fixed to the annular member, and a third annular member, having a threaded part on a radially inner wall, which is relatively rotated to said second annular member, said case member having a threaded part, engaging with said threaded part of said third annular member of said adapter, at a first portion on a radially outer wall of said case member, thereby moving said case member in the axial direction within adapter, by rotation of said third annular member without rotating said case member.

5. An intracranial pressure transducer according to claim 4, wherein:

said supporting member comprises a first supporting member comprising a square plate having a circular hole at a central part thereof and which is made of crystallization glass having the same thermal expansion rate as that of a semiconductor silicon single crystal and to which said strain sensing member is bonded in order to close said circular hole of said first supporting member, and a second supporting member comprising an annular member, the diameter of a radially outer wall of which corresponds to that of a radially inner wall of said casing and a radially inner wall of which is formed as the funnel shape, the diameter of said throttle hole being larger than that of said circular hole of said first supporting member.

6. An intracranial pressure transducer according to claim 5, wherein:

said strain sensing member comprises a N-type silicon single crystal, and said strain sensitive elements comprise two pair of P-type region integrally formed respectively at a central part and a peripheral part on a strain sensitive region corresponding to said circular hole of said first supporting member on said N-type silicon single crystal composing said strain sensing member by the diffusion method to form a Wheatstone bridge, said regions being respectively connected to form the wheatstone bridge by lead wires.

7. An intracranial pressure transducer according to claim 6, wherein:

said indicating circuit, connected to said two pair of said strain sensitive elements through connector means including five pins equipped with a top portion of said case member, comprises;

a power source for supplying predetermined D.C. voltage to a third connection of said wheatstone bridge through a variable register for adjusting the voltage and fourth pin of said connector means, a slide register for adjusting the zero balance connected to said second and third pins for forming a second connection of said wheatstone bridge, a temperature compensating circuit, comprising a fixed resistor and a thermistor respectively connected in series, connected to a slide tap of said slide register, a differential amplifier comprising the operational amplifier one input terminal of which is connected to said temperature compensating circuit and a second input terminal of which is connected to a fifth pin of said connector means connected to said fourth connection of said wheatstone bridge, a recorder connected to an output terminal of said differential amplifier through a variable capacitor for cutting the D.C. component, and a D.C. voltage meter connected to said output terminal of said differential amplifier through a smoothing circuit comprising a choke coil and two capacitors grounded, and a first pin of said connector means connected to a first connection of said wheatstone bridge, grounded.

8. An intracranial pressure transducer according to claim 7, wherein:

the dimensions of said strain sensing member is 0.038 mm thickness, 5 mm width and 6 mm length, said second supporting member is made of stainless steel, said adapter and casing member of said casing are made of stainless steel, and said pressure receiving layer comprises silicon rubber.

9. An intracranial pressure transducer according to claim 2, wherein:

said adapter of said casing has a tapered outer wall having said screwed part and a plurality of radial grooves on said first flat portion, and said case member of said casing comprises a T-shaped annular member having a hole for introducing atmosphere pressure therein, a radially outer diameter of a leg portion of which is smaller than an inner diameter of said adapter in order to maintain the predetermined clearance connected to said plurality of radial grooves, and a flange portion of which is fixed to said first flat portion of said adapter by bolt means in order to maintain the second portion of said leg portion of said case member to be projected a predetermined length from the second portion of said adapter.

10. An intracranial pressure transducer according to claim 9, wherein:

said supporting member comprises a first supporting member comprising a square plate having a circular hole at a central part thereof, and which is made of crystallization glass having the same thermal expansion rate as that of a semiconductor silicon single crystal and to which said strain sensing member is bonded in order to close said circular hole of said first supporting member, and a second supporting member comprising an annular member, the diameter of a radially outer wall of which corresponds to that of a radially inner wall of said casing and a radially inner wall of which is formed as the funnel shape, the diameter of said throttled hole being larger than that of said circular hole of said first supporting member.

11. An intracranial pressure transducer according to claim 10, wherein:
said strain sensing member comprises a N-type semiconductor silicon single crystal, and two pair of said strain sensitive elements comprise P-type regions integrally formed respectively at a central part and a peripheral part on a strain sensitive region corresponding to said circular hole of said first supporting member on said strain sensing member of said N-type semiconductor silicon single crystal by the diffusion method, said regions being respectively connected in order to form wheatstone bridge by lead wires.

12. An intracranial pressure transducer according to claim 11, wherein:
said indicating circuit, connected to said two pair of said strain sensitive elements through connector means including five pins equipped with said flange part of said case member, comprises;
a power source for supplying predetermined D.C. voltage to a third connection of said wheatstone bridge through a variable register for adjusting the voltage and fourth pin of said connector means,
a slide register for adjusting the zero balance connected to said second and third pins for forming a second connection of said wheatstone bridge,
a temperature compensating circuit, comprising a fixed resistor and a thermistor respectively connected in series, connected to a slide tap of said slide register,
a differential amplifier comprising the operational amplifier one input terminal of which is connected to said temperature compensating circuit and a second input terminal of which is connected to a fifth pin of said connector means connected to said fourth connection of said wheatstone bridge,
a recorder connected to an output terminal of said differential amplifier through a variable capacitor for cutting the D.C. component, and
D.C. voltage meter connected to said output terminal of said differential amplifier through a smoothing circuit comprising a choke coil and two capacitors grounded, and
a first pin of said connector means connected to a first connection of said wheatstone bridge, grounded.

13. An intracranial pressure transducer according to claim 12, wherein:
the dimensions of said strain sensing member is 0.038 mm thickness, 5 mm width and 6 mm length;
said second supporting member is made of stainless steel,
said adapter and case member of said casing are made of stainless steel, and
said pressure receiving layer comprises silicone rubber.

14. An intracranial pressure transducer according to claim 1, wherein:
said casing includes an annular passage communicating with the exterior of the transducer for discharging a body fluid from the body and blood between the skull and dura to the exterior of said transducer; thereby preventing the filling and the coagulation of the body fluid and blood between the skull and dura, and attaining accurate measurement of the intracranial pressure.

15. An intracranial pressure transducer according to claim 14, wherein:
said casing comprises an adapter including said annular member and a case member which encloses said pressure-electric transducing portion and is inserted within a radially inner wall of said adapter and is fixed to said adapter at a first portion thereof in order to provide that a second portion of said case member protrudes from a second portion of said adapter a predetermined length;
said annular passage is formed by a clearance between a radially inner wall of an adapter and a radially outer wall of a case member of said casing.

16. An intracranial pressure transducer according to claim 1, wherein:
said strain sensitive element comprises a diffused strain gauge formed on the surface of said strain sensing member by the diffusion method.

17. An intracranial pressure transducer according to claim 1, wherein:
said strain sensing member is of a N-type semiconductor silicon single crystal, and
said strain sensitive element comprises at least two P-type regions integrally formed at the central portion on said N-type semiconductor silicon single crystal by the diffusion method.

18. An intracranial pressure transducer according to claim 1, wherein:
said supporting member comprises a first supporting member comprising a square plate having a circular hole at a central part thereof and which is made of crystallization glass having the same thermal expansion rate as that of a semiconductor silicon single crystal and to which said strain sensing member is bonded in order to close said circular hole of said first supporting member, and a second supporting member comprising an annular member, the diameter of a radially outer wall of said second supporting member corresponding to that of a radially inner wall of said casing and a radially wall of said second supporting member being formed as the funnel shape, the diameter of said throttled hole being larger than that of said circular hole of said first supporting member.

19. An intracranial pressure transducer according to claim 1 wherein:
said strain sensitive member comprises a foil gauge bonded on the surface of said diaphragm.

20. An intracranial pressure transducer according to claim 1, wherein:
said strain sensitive member comprises a differential transformer means in which a core connected to said strain sensing member is movable in the axial direction within a pair of coils.

* * * * *